US006379920B1

(12) United States Patent
El-Sayed et al.

(10) Patent No.: US 6,379,920 B1
(45) Date of Patent: Apr. 30, 2002

(54) SPECTROSCOPIC DIAGNOSTICS FOR BACTERIA IN BIOLOGIC SAMPLE

(75) Inventors: Mostafa A. El-Sayed, Atlanta, GA (US); Ivan H. El-Sayed, Somerville, MA (US)

(73) Assignees: Georgia Tech Research Corp., Atlanta, GA (US); Boston Medical Center Corp., Boston, MA (US)

( * ) Notice: Subject to any disclaimer, the term of this patent is extended or adjusted under 35 U.S.C. 154(b) by 0 days.

(21) Appl. No.: 09/624,059

(22) Filed: Jul. 24, 2000

Related U.S. Application Data

(60) Provisional application No. 60/145,522, filed on Jul. 24, 1999.

(51) Int. Cl.$^{7}$ ........................ C12Q 1/16; C12Q 1/24; C12Q 1/02; C12Q 1/00

(52) U.S. Cl. ........................ 435/34; 435/30; 435/29; 435/4

(58) Field of Search ........................ 435/34, 30, 29, 435/4

(56) References Cited

U.S. PATENT DOCUMENTS 5,660,998 A * 8/1997 Naumann et al.

FOREIGN PATENT DOCUMENTS

WO WO 97/48329 A1 12/1997
WO WO 98/41842 A1 9/1998

OTHER PUBLICATIONS

WO 99/16895. Ismail et al, 04–1999. Use of universal culture medium FTIR spectrometry.*

Sorrell et al. (1994). Bacteria identification of otitis media with fluorescence spectroscopy. Lasers in Surgery and Medicine 14: 155–163.*

Werhaven et al. (1994). Non–invasive optical diagnosis of bacteria causing otitis media. Laryngoscope 104: 264–268.*

* cited by examiner

*Primary Examiner*—Ralph Gitomer
*Assistant Examiner*—Mahreen Chaudhry
(74) *Attorney, Agent, or Firm*—Todd Deveau; Charles Vorndran; Troutman Sanders LLP

(57) ABSTRACT

A method to analyze and diagnose specific bacteria in a biologic sample using spectroscopy is disclosed. The method includes obtaining the spectra of a biologic sample of a non-infected patient for use as a reference, subtracting the reference from the spectra of an infected sample, and comparing the fingerprint regions of the resulting differential spectrum with reference spectra of bacteria in saline. Using this diagnostic technique, specific bacteria can be identified sooner and without culturing, bacteria-specific antibiotics can be prescribed sooner, resulting in decreased likelihood of antibiotic resistance and an overall reduction of medical costs.

26 Claims, 3 Drawing Sheets

SPECTROSCOPIC DIAGNOSTICS FOR BACTERIA IN BIOLOGIC SAMPLE

This application claims priority to U.S. provisional application no. 60/145,522, filed on Jul. 24, 1999.

This invention is the subject of a grant from the United States Department of Energy, Grant No. #DEFG0297ER14799. The U.S. government may have certain rights in this invention.

BACKGROUND OF THE INVENTION

1. Field of the Invention

The present invention relates to using spectroscopic methods in medical diagnostics to analyze and diagnose specific bacteria in a biologic sample. Using this diagnostic technique, specific bacteria can be identified sooner and without culturing, and bacteria-specific antibiotics can be prescribed sooner, resulting in an earlier, more accurate diagnosis of infection and corresponding antibiotic prescription, decreased likelihood of antibiotic resistance and an overall reduction of medical costs.

Middle ear infection, or otitis media (OM), is the most frequent diagnosis in children. Seventy-five percent of children under age three experience at least one episode of otitis media, while almost half of those children will have three or more infections.

OM accounts for almost 46% of the more than 48 million annual prescriptions in the United States. The estimated cost of treating OM is about $5 billion annually.

OM is a bacterial infection that results in inflammation of the inner ear and an accumulation of fluid behind the eardrum. Usually resulting from a bacterial or viral infection secondary to a cold, sore throat, or other respiratory infection, OM is usually treated with antibiotics. A diagnosis of the specific bacteria results in targeted treatment by helping physicians prescribe an antibiotic effective for the particular bacteria.

Current medical methods used to diagnose bacterial organisms normally require at least one day. In addition, physicians often need to determine bacteria resistance to antibiotics, and this determination routinely takes another day. Gram staining, analyzing organisms from a sample visually with a microscope, may provide a rough estimate of the most likely organism, but this process can be inaccurate. This is especially so for one of the bacteria common to OM, *Haemophillus influenzae*. Thus, after a presumptive diagnosis from gram staining, the bacteria are cultured for at least a day and identified. This time-intensive process follows the difficulty of acquiring the sample from the patient. The methods of collection depend on the site of infection. Some are readily accessible, such as urine, however some samples require invasive procedures which can be quite painful, including, in the case of OM, piercing the eardrum to withdraw infected fluid. Additionally and unavoidably, some samples are collected after the patient has begun antibiotic treatment, making diagnosis of the bacteria organism difficult or impossible.

Because of the delay in specific bacterial diagnosis and the pain suffered by the patient, physicians usually prescribe broad spectrum antibiotics that can cover a wide variety of bacteria until the specific strain of bacteria is identified. After identification, the antibiotics are usually changed to those necessary to treat the infection. In the case of OM, the physician will treat with antibiotics to cover the most likely organisms, and if the organism is resistant to the antibiotic, the physician will change the antibiotic after the patient fails to improve over a few days. In cases where a specific bacterial diagnosis is impossible, treatment with broad spectrum antibiotics is continued.

There is a growing concern in the medical field over developing antibiotic resistance. Bacteria can develop resistance to antibiotics when they are exposed to them through several mechanisms. They also have the ability to pass this resistance on to other bacteria that have not been exposed to the antibiotic. As a result, physicians prefer to use the simplest antibiotic necessary to treat an infection, thus reducing the exposure of bacteria to stronger antibiotics and theoretically reducing the rate of resistance.

Therefore, there exists a need in the art for methods for rapidly diagnosing bacteria, thus improving patient care by providing targeted antibiotic therapy earlier. Rapid diagnostic tests can decrease antibiotic resistance by decreasing the use of broad spectrum and ineffective antibiotics. Medical costs may also be lowered since fewer prescriptions would be changed during treatment.

2. Prior Art

Some spectroscopic techniques already known in the art have been adapted for use in medical diagnostics, none of which provides the advantages of the present invention. For example, WO 97/48329 discloses a method for diagnosing cervical precancer using near infrared Raman spectroscopy. Additionally, several spectroscopic techniques are already used to detect bacteria in isolated samples.

Goodacre et al. disclose the use of pyrolysis mass spectrometry (PyMS), Fourier transform infrared spectroscopy (FTIR) and dispersive Raman microscopy to analyze a group of bacterial isolates associated with urinary tract infections. (*Microbiology* May 1998, 144 (Pt.5): 1157–70).

WO 98/41842 discloses a system for the detection of bacteria antibody complexes using UV resonance Raman spectroscopy. The system uses Raman spectroscopy to create a characteristic spectral peak of a microorganism analyzed from an antibody complex.

Werkhaven et al. disclose that an optical window that will transmit sufficient light for in vivo measurement of fluorescence profiles has been found in the chinchilla tympanic membrane. (*Laryngoscope* March 1994; 104(3 pt. 1): 264–8).

Sorrell et al. disclose that fluorescence profiles of four common pathogens have been determined and are reproducible. (*Lasers Surg Med* 1994; 14(2): 155–63.

Timmins et al. disclose that distinct fingerprints for three Candida species are consistent with reference isolates. (*J. Clin. Microbiol.* February 1998, 36(2): 367–74).

In the above studies, the identification of bacteria using Fourier-transfer infrared spectroscopy (FTIR) has only been demonstrated for isolated bacteria after they have been cultured and purified. The ability of FTIR spectroscopy to detect bacteria in biologic fluid has not, heretofore, been investigated.

Biologic fluid has absorption bands that greatly overlap the regions useful in differentiating the differences in bacteria. Such overlap would greatly change the previous general analysis and conclusions of the spectroscopic techniques. Furthermore, the biologic fluid might interact chemically with the chemicals in the bacteria or alter the local environment of the bacteria (i.e., by changing the pH) sufficiently to alter the spectra of the bacteria and make them unrecognizable when compared to their pure spectra. Therefore, it is necessary to be able to study the spectra of the bacteria in the biologic fluid, that is, in samples taken directly from the patient. In addition, it becomes more practical to analyze the spectra of bacteria within the context of one disease entity at a time. This specifies the nature of the medium and simplifies data interpretation by limiting the number of possible pathogens. None of the above-described techniques address these considerations.

The present invention, on the other hand, is directed to a method for using spectroscopy in the identification of specific bacteria in a biologic sample. Preferably, FTIR is used to detect the three most common bacteria in otitis media (OM), *Streptococcus pneumoniae* (SP), *Haemophilus influenzae* (HI) and *Morazella catarrhalis* (MC).

SUMMARY OF THE INVENTION

Briefly described, in a preferred form, the object of the present invention is to provide a method for the diagnosis of a bacterial organism in a biologic fluid using spectroscopic techniques. Preferably, FTIR, fluorescence and Raman spectroscopy are used as medical diagnostics to detect the three most common bacteria in otitis media (OM), *Streptococcus pneumoniae* (SP), *Haemophilus influenzae* (HI) and *Morazella catarrhalis* (MC).

It is a further object of this invention to provide a diagnostic method for detecting specific strains of bacteria in a biologic sample without subjecting the sample to culturing. Preferably, FTIR, fluorescence and Raman spectroscopy are used to detect bacteria. More preferably, FTIR is used to diagnose the bacteria.

It is another object of the present invention to improve the treatment of infectious diseases by providing a rapid strain-specific bacterial diagnosis. By increasing the speed of diagnosis of the specific strain, a doctor may immediately begin targeted treatment of the infection with an antibiotic specific to that strain.

These objects have been achieved by using spectroscopic techniques such as FTIR, fluorescence and Raman spectroscopy to compare the known spectra of particular bacteria strains with the spectrum determined from a biologic sample and subtracting the spectrum of pure serum.

More particularly, the present invention is directed to a method for diagnosing bacteria in a biologic sample comprising analyzing a sample of infected serum with a spectrometer, subtracting the spectrum of a previously-obtained reference serum from the spectra of the infected serum, and comparing the resulting differential spectra with reference spectra of bacteria in saline to determine the specific bacteria present in the sample.

It has been found that using our spectroscopic techniques, a rapid determination of the specific bacterial strains can be made, thus allowing for targeted treatment and avoiding the use of broad spectrum antibiotics. Such targeted treatment eliminates the medical costs associated with prescribing broad spectrum antibiotics and then represcribing antibiotics specific to the infection. Additionally, targeted treatment reduces the likelihood of the patient developing antibiotic resistance.

These and other objects, features, and advantages of the present invention will become more apparent upon reading the following specification in conjunction with the accompanying drawing figures.

DETAILED DESCRIPTION OF THE PREFERRED EMBODIMENT

Figure 1:
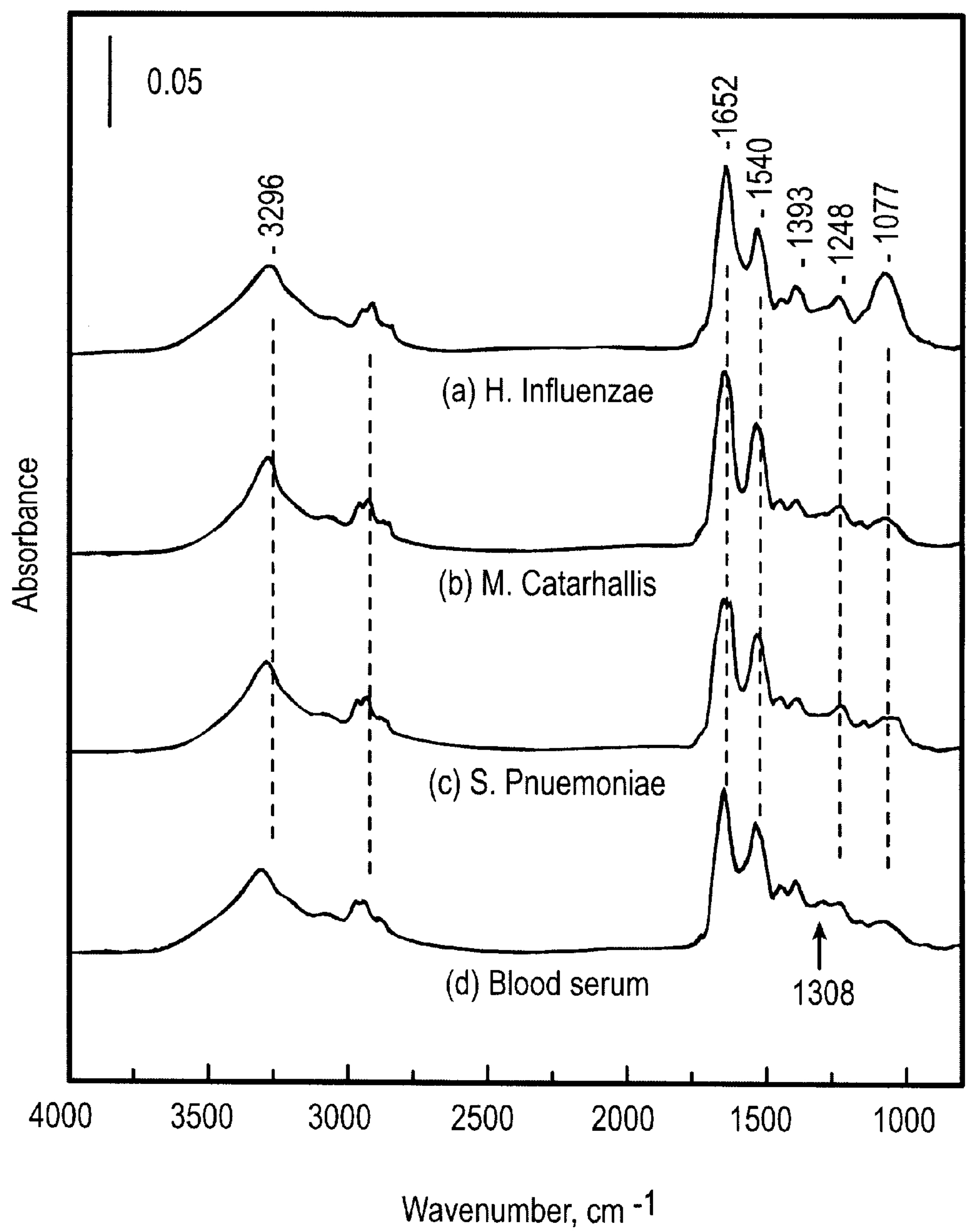
FIG. 1 is a graph of absorbance versus wavelength which shows the FTIR spectra of the three bacterial dry films (a) *Haemophilus influenzae* (HI), (b) *Morazella catarrhalis* (MC), and (c) *Streptococcus pneumoniae* (SP) and for (d) serum in the spectral region of 4000–800 $cm^{-1}$.

A rapid test to identify bacteria causing infections while still submerged in biologic fluid has been discovered using spectroscopy, including Fourier Transfer Infrared Spectroscopy (FTIR), fluorescence or Raman spectroscopy. Spectroscopic techniques can be used to significantly decrease the processing time of samples from the moment a sample is collected until the time a diagnosis can be made. Once the spectral regions useful for identification are determined, it is possible to develop both noninvasive and invasive techniques for diagnosing organisms while still in the body using laser-fiber optic methodology.

For example, spectroscopic techniques can be incorporated into rapid, automated systems that can process large numbers of cultured bacteria from any collected sample. Additionally, bacteria can be diagnosed in freshly collected samples while still contained in fluid from the human body, for example middle ear aspirates, pus, pleural effusions, synovial fluid, abscesses or cavity swabs. It is also possible to diagnose microorganisms in body cavities using spectroscopic techniques by passing and receiving the optical signal through epithelial tissues using fiberoptic systems. Spectroscopic techniques can also be integrated into fiberoptic instruments such as endoscopes, bronchoscopes, arthroscopes and flexible endoscopes used in gastrointestinal and colonoscopy procedures to detect infection in the body cavity.

Using the method of the present invention, a laser spectroscopic technique for identifying bacteria in vivo can be developed. The laser is passed through a fiber optic system, and the signal is received through the same system. Using the spectroscopic regions determined by the method of the present invention, bacteria can be distinguished from other bacteria and from bodily fluids.

Additionally, the unique regions for each bacterium discovered through the process of the present invention can be incorporated into an automated system to identify bacteria more quickly. Such automation would eliminate the need for bacteria culturing and allow for rapid diagnosis using only a small sample.

Spectroscopic methods of diagnosis are known to be rapid and can be automated to test multiple samples at a time. Fluorescence, absorption in the ultraviolet (UV), visible and infrared (IR) regions and laser Raman spectroscopy are the most common spectroscopic techniques and are all contemplated for use in the method of the present invention.

A preferred embodiment of the present invention is the use of FTIR to diagnose bacteria in a biologic sample. FTIR offers a rapid, inexpensive, accurate and potentially automated method for the detection of bacteria. FTIR spectroscopy provides a fingerprint spectrum of molecules based on the vibration of the chemical bonds present that is specific to the structure of those molecules in a given substance. Using cluster analyses or artificial neural network analyses or developing a database of known bacterial spectra, a rapid, automated system may be used to identify bacteria isolated in clinical settings.

Bacteria represent a large population of organisms comprised of many different species. Since bacteria are biologic cellular organisms, they contain many chemicals in common with other cellular organisms such as amino acids, nucleotides and polysaccharides. The human body also contains many of these chemicals within its cells as well as in the extracellular space. Thus, many bodily fluids are expected to contain chemicals that are similar to those found in bacteria. Spectroscopically, this means that it is expected that many features in the spectroscopic analysis will appear similar when comparing different bacteria and when comparing human cells and bodily fluid. However, distinctions between each bacteria and between bacteria and human cells do exist. The ability to exploit these differences in a manner which makes them detectable is the subject of the present invention.

Changes in the local environment of a chemical, in the sequence of an amino acid, or even in the relative ratio of one chemical to another in a specific bacteria may be detected spectroscopically. These differences can be exploited to identify individual bacteria.

Bacteria can be sampled from many forms of biologic sera. For example, middle ear aspirate can be obtained by tympanocentesis, saliva can be obtained through swabbing or sampling, or blood can be drawn. Examples of biologic fluids useful in the method of the present invention include, but are not limited to, blood, urine, middle ear aspirate, bile, vaginal secretions, pus, pleural effusions, synovial fluid, abdominal cavity abscesses, and saliva.

The following examples are designed to study one disease process at a time, merely for ease in data interpretation. In the same manner that a physician selects the most likely organisms to begin treatment, analysis of spectra can be simplified by reducing the number of expected possible bacteria to the common bacteria that cause a certain disease. In this manner, analysis algorithms for each disease can be developed.

The following examples are provided to demonstrate the present invention and are not intended to limit its scope in any way.

EXAMPLE I

Otitis media (OM) is one of the most common infectious diseases. Treatment of OM is estimated at $5 billion annually in the United States. OM represents an infection in the middle ear, behind the tympanic membrane, and can exist as an acute otitis media (AOM) or as a chronic nonpurulent effusion known as otitis media with effusion (OME). The fluid of AOM can range from a watery serous effusion to frank pus with many inflammatory cells, products and debris. OME can result after an episode of AOM or develop on its own with a silent onset, and the fluid can range from a watery serous effusion to a viscous form containing mucin. Three bacteria are most consistently cultured from sampled effusions of AOM and OME: *Streptococcus Pneumonia* (SP), *Haemophilus Influenza* (HI) and *Moraxella Catarhallis* (MC). In this example, we examined the FTIR spectra of these bacteria in blood serum.

Sample: Three bacterial species grown in culture broth, HI (ATCC 49247), SP (ATCC 046196), MC (clinical isolate), and blood serum collected from a healthy volunteer in a standard fashion and stored frozen, were used for this study. The final bacteria concentration were estimated to be $1.2\times10^6$ cell/ml, in physiological saline. This was comparable to the concentration of bacteria in the fluid of infected persons. The mixtures of each bacterial species with blood serum were prepared at volume ration of 1:1. Here bacterium was at the above concentration and the blood serum was at the original concentration as separated from the blood sample from the volunteer. This resultant final concentration of bacteria in serum was $8.0\times10^5$ cells/cm$^2$.

A droplet of ~0.2 ml from each sample at the above concentrations was placed on a ZnSe plate to make an area of ~0.5 cm$^2$. To remove spectral interference from water, samples were dried overnight at room temperature and then heated at 50° C. for ~10 minutes for further dehydration. The samples of pure serum, isolated bacteria, and mixtures of serum and bacteria were prepared in the same manner.

FTIR spectroscopy: A Bruker IFS66/S infrared spectrometer was used, with a DTGS detector used for the mid- to far-IR region. All spectra were the average of 100 scans at a resolution of 2 cm$^{-1}$. Baseline correction and spectral subtraction were obtained using OPUS 2.0 software provided by Bruker. Spectral subtraction between the bacterium-serum mixture and pure serum was judged by selecting a specific band only found in blood serum and ensuring that this band had completely disappeared in the difference spectrum. The chosen band was at 1307 cm$^{-1}$, and it was not present in the spectra of any of the bacteria.

Results: Steady-state spectra: FIG. 1 shows the FTIR spectra of the three bacterial dry films, HI (a), MC (b), and SP (c), and for serum (d) in the spectral region of 4000–800 cm$^{-1}$. Three common spectral features were found: a broad band at 3300 cm$^{-1}$ (which can be assigned to the well-known amide A band, resulting from the N—H stretching vibration of polypeptide chain); two bands at 1651 cm$^{-1}$ and 1540 cm$^{-1}$, which can be assigned to the amide I and II modes of the protein, respectively. These band features are associated with the cellular proteins. The observed bands between 1300 and 800 cm$^{-1}$ can be attributed to the specific absorption of the phosphate groups and possible oligo- and polysaccharides of the cell wall (van der Meir). The DNA/RNA oligo- and polynucleotides (base-ring vibrations of guanine, thymine, adenine, cytosine and uracil) were also observed in the region between 1700–1200 cm$^{-1}$. Possible band assignment of these compounds in bacteria has been reported previously in a Raman study by Naumann. A careful comparison of the spectra in this region could serve as a fingerprint for each bacterium since their chemical composition is not exactly the same. The blood serum in FIG. 1 has a similar spectral feature as those for bacteria. There is almost a one-to-one correlation between the four spectra shown in FIG. 1. However, significant difference does exist in the fingerprint region. For example, the band at 1307 cm$^{-1}$ is a unique band for serum. This band is used in the spectral subtraction of the serum spectrum from the spectra of the bacteria in serum in order to characterize the spectra of the different bacteria in the serum medium (as a biologic fluid).

Figure 2A:
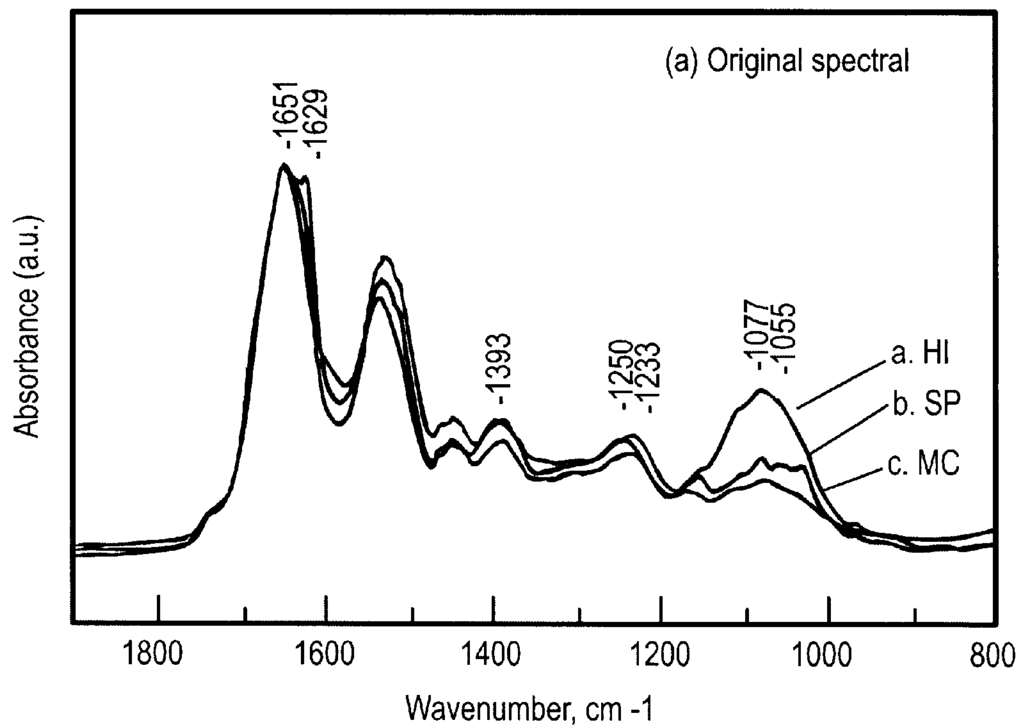
FIG. 2*a* is a graph of absorbance versus wavelength which depicts the three bacterial species (a) *Haemophilus influenzae* (HI), (b) *Morazella catarrhalis* (MC), and (c) *Streptococcus pneumoniae* (SP) in direct comparison with their "row" infrared (IR) absorption in the region of 1800 and 1700 $cm^{-1}$.
Figure 2B:
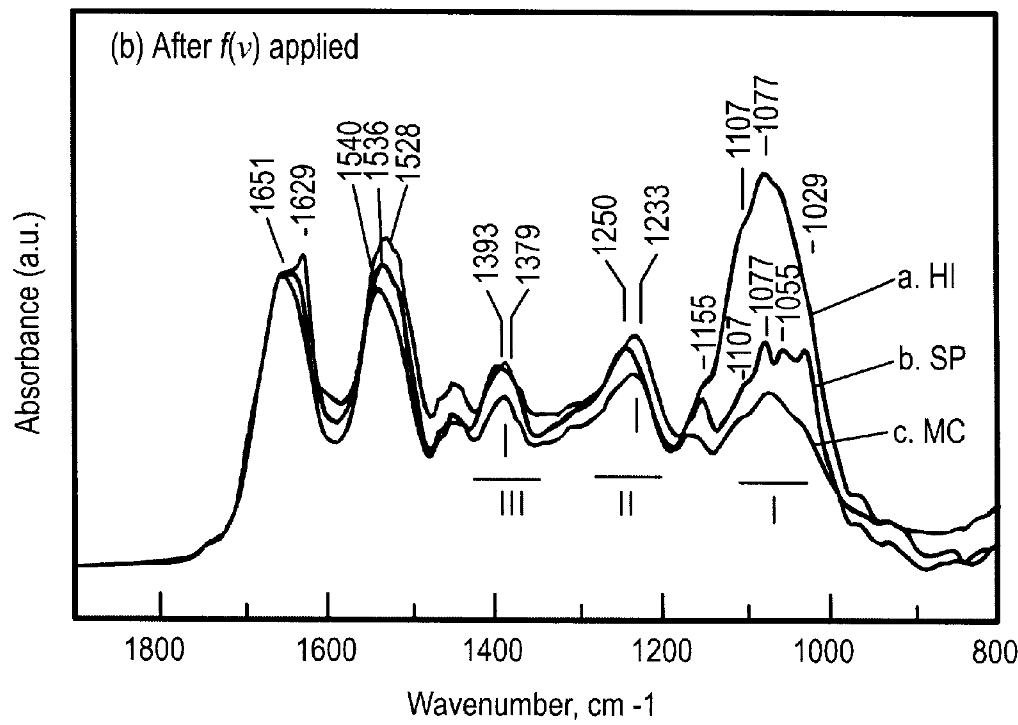
FIG. 2*b* depicts the three bacterial species (a) *Haemophilus influenzae* (HI), (b) *Morazella catarrhalis* (MC), and (c) *Streptococcus pneumoniae* (SP) in direct comparison with their infrared (IR) absorption after application of a function f(n), which increases the intensity of the lower frequency bands in the fingerprint region.

As shown in FIGS. 2*a* and 2*b*, these three bacteria species can be easily identified by direct comparison of their IR absorption. The mixture of bacteria and serum will be presented in Example II below.

Comparison of the fingerprint region: FIG. 2*a* shows the direct comparison of the "row" spectra of the three bacteria in the region of 1800 and 1700 $cm^{-1}$. The important characteristic differences in the spectra of these bacteria in this region are as follows:

1. A distinction between HI and the other two bacteria can be made from the large difference in the intensity of the band in the 1000–1150 $cm^{-1}$ region. This band is more intense for the HI than for either SP or MC. For example, for HI, the relative intensity of this band to the bands in the 1200–1300 $cm^{-1}$ region is more than 2, and almost 3. For MC, this ratio is slightly greater than one.
2. In order to distinguish between SP and MC, the FTIR spectrum of SP bacterium is characterized by being sharper (better resolved) in the 1100–1000 $cm^{-1}$, and the amide I band (in the 1620–1660 $cm^{-1}$ region) of the SP bacterium is split (again due to its higher resolved sharper spectrum). In order to enhance the relative intensity of the fingerprint region in the 1100–1000 $cm^{-1}$, relative to the more intense amide bands in the 1700–1500 $cm^{-1}$ region, each of the spectrum in FIG. 2*a* is multiplied by a function, f(n), that increases the intensity of the lower frequency bands more than the higher frequency ones: $f(n)=(1.7-n/1000)\times100$. After applying this function to the absorbance, An, at frequency n of each bacterium, the new absorbance, An*, becomes $An^*=An\times f(n)$. This is applicable in the frequency range between 1700 and 1000 $cm^{-1}$. By applying this function, the enhanced spectra are shown in FIG. 2*b*. It is shown that after this treatment, the spectral difference becomes more obvious. Three band groups are labeled as I, II and III. In group I, there is only an unresolved broad band for HI and MC, whereas there are a few distinct bands for SP, at 1077, 1057 and 1029 $cm^{-1}$. In the band groups II and III, the band maximum is different in these species, as shown in the figure: 1250 $cm^{-1}$ (HI), 1233 $cm^{-1}$ (MC and SP). There is also a band shape and band position difference in group III, ~1393 $cm^{-1}$ for HI, and ~1379 $cm^{-1}$ for MC and SP.

EXAMPLE II

In order to see if the signatures differentiating the spectra of the different bacteria persist in biologic fluid, the spectra of these bacteria were taken in serum. The spectrum of pure serum previously obtained was then subtracted from the spectra of the samples containing bacteria mixed in serum and the remaining spectra were then compared with the spectra of bacteria in saline shown in FIG. 2*a*.

Bacteria and serum have similar band features in the region of 4000–800 $cm^{-1}$, as shown in FIG. 1. Efforts have been made to characterize the bacteria in the environment of blood serum. As described in the experimental section, the mixture of bacterium and serum contains 1:1 volume ratio of the concentrated bacterial solutions (~$1.2\times10^6$ cell/ml) and the original serum extracted from the blood that is donated by a healthy volunteer. Dry films were made by controlled amounts of aqueous solutions containing mixtures of each bacterium with the blood serum.

Figure 3A:
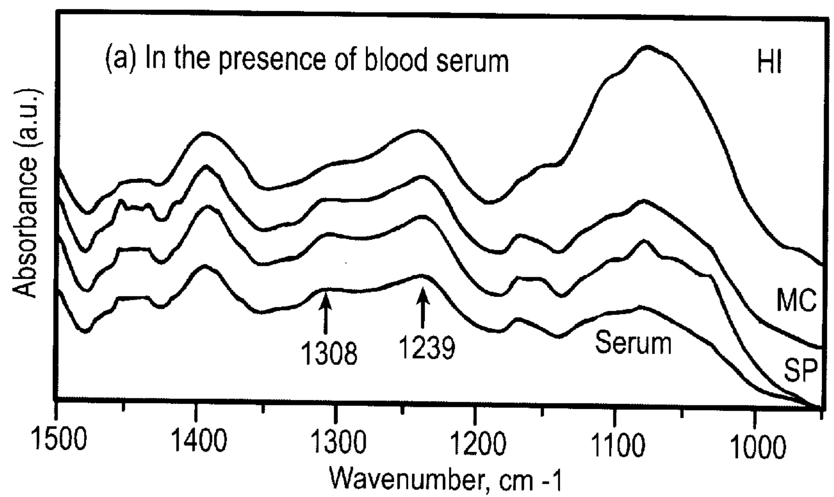
FIG. 3*a* is a graph of absorbance versus wavelength which shows the spectral comparison of the serum and each bacterium in the presence of the serum in the spectral region of 1500–950 $cm^{-1}$.

FIG. 3*a* shows the spectral comparison of the serum and each bacterium in the presence of the serum in the spectral region of 1500–950 $cm^{-1}$. In this region, the original bands and their positions for each bacterium were still observable. In other words, bacteria do not lose their IR band features, even when mixed with serum. The contribution of serum in the infrared spectrum may be subtracted in order to reveal the typical fingerprints of each bacterium. The criteria for a complete removal of blood serum was measured by the disappearance of the band at ~1308 $cm^{-1}$, which is unique for serum, as shown in FIG. 1. The band at ~1239 $cm^{-1}$ could also be used as an additional band since the relative intensity of these two bands is comparable in the case of blood serum, whereas it is not in the case of the three bacteria (FIG. 1). The band at ~1239 $cm^{-1}$ is relatively weak in the spectrum of each bacterium.

Figure 3B:
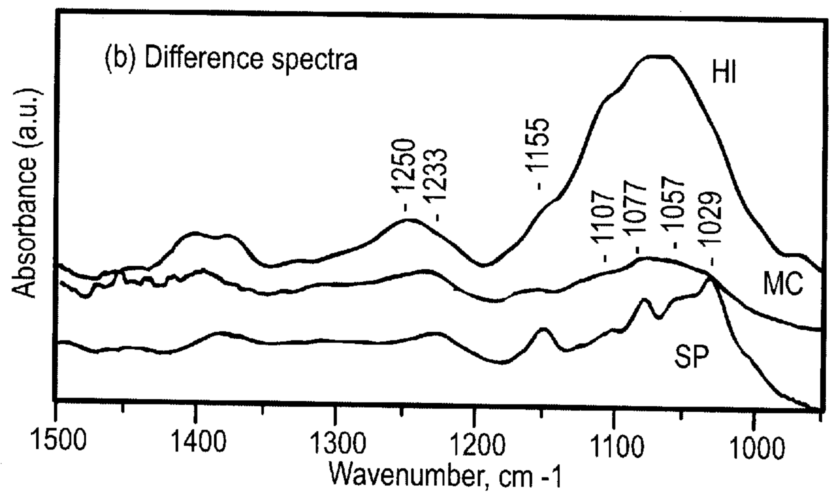
FIG. 3*b* depicts the difference spectra in the region of 1500–950 $cm^{-1}$ of each bacterium when compared with the pure bacteria spectra.
Figure 3C:
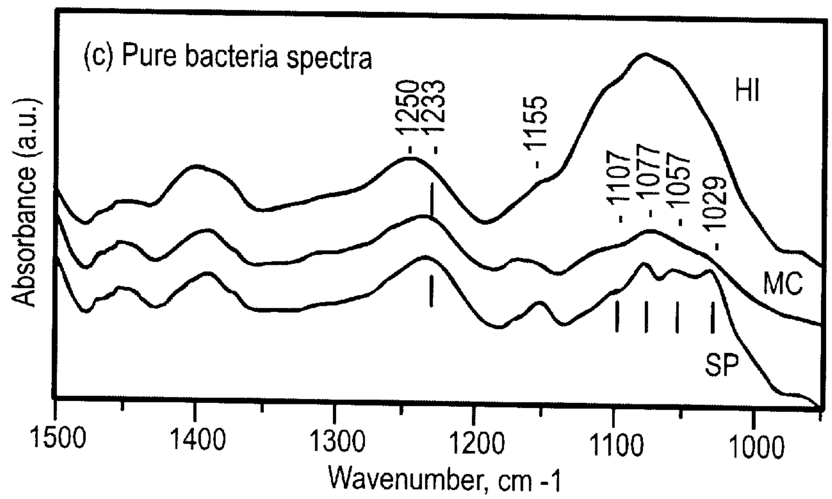
FIG. 3*c* depicts the pure bacteria spectra in the region of 1500–950 $cm^{-1}$.

In FIG. 3*b*, the difference spectra in the region of 1500–950 $cm^{-1}$ clearly show the original band features of each bacterium when compared with the pure bacteria spectra (shown in FIG. 2*b*). This study demonstrates that no significant spectroscopic reaction occurs between the serum and the bacteria as demonstrated by the additivity of their FTIR spectra. This result demonstrates that one is able to distinguish these three bacteria in the presence of blood serum. A simple method for rapid identification of bacteria in blood serum is thus possible.

From the above results, it is concluded that in the FTIR spectra of dry film, each bacterium has a typical band feature in the region of 700–1800 $cm^{-1}$. Furthermore, the spectra were found not to change when the bacteria are present in serum (which mimics the biologic fluid). Three groups were analyzed and could serve as the fingerprints for the rapid identification and characterization. The identification can be carried out visually for small groups of bacteria, or better yet, with a software program that analyzes the relative intensities, band shapes and frequencies in this region. This will give much better statistics and thus higher confidence factors for the diagnosis.

While the invention has been disclosed in its preferred forms, it will be apparent to those skilled in the art that many modifications, additions, and deletions can be made therein without departing from the spirit and scope of the invention and its equivalents as set forth in the following claims. For example, while dry film was used for analysis, the actual solution can be used directly in an attenuated total reflectance (ATR) cell. In this cell, the strong absorption of water can be minimized. The different infrared spectral regions of the signature of the different bacteria using this method of detection have also been identified.

What is claimed is:

1. A method for detecting bacteria in a biologic fluid sample comprising the steps of:

a. obtaining absorption spectra directly from an uncultured biologic fluid sample;

b. subtracting absorption spectra of a reference sample from the absorption spectra of the biologic fluid sample to form a differential spectra;

c. analyzing the differential spectra to detect the presence of bacteria in the sample.

2. The method of claim 1, further comprising the step of:

d. identifying bacteria detected in the biologic fluid sample by comparing the differential spectra with reference spectra of bacteria.

3. The method of claim 1, wherein the absorption spectra is obtained in the regions selected from the group consisting of ultraviolet (UV), visible and infrared (IR).

4. The method of claim 1, wherein the absorption spectra is obtained using an instrument selected from the group consisting of a Fourier transform infrared spectrometer, a fluorometer and a Raman spectrometer.

5. The method of claim 2, wherein the reference spectra is spectra of bacteria selected from the group consisting of *Haemophilus influenzae* (HI), *Morazella catarrhalis* (MC), and *Streptococcus pneumoniae* (SP).

6. The method of claim 1, wherein the biologic fluid sample is selected from the group consisting of a blood, saliva, urine, bile, vaginal secretions, middle ear aspirate, pus, pleural effusions, synovial fluid, abscesses, cavity swabs, and serum.

7. The method of claim 1, wherein the biologic fluid sample is contained in fluid from the human body.

8. The method of claim 2, wherein the identity of the bacteria is determined from absorption spectra in the region of 700–1800 $cm^{-1}$.

9. The method of claim 1, wherein either dry film or an attenuated reflectance cell are used for analyzing the sample.

10. A method for decreasing the time for diagnosing a bacterial strain infection comprising the steps of:

a. obtaining the absorption spectra of an uncultured biologic fluid sample;

b. subtracting the absorption spectra of a previously-obtained reference sample from the absorption spectra of the uncultured biologic fluid sample to obtain a differential spectra;

c. analyzing the differential spectra to detect the presence of bacteria in the sample.

11. The method of claim 10, further comprising the step of:

d. identifying bacteria detected in the biologic fluid sample by comparing the differential spectra with reference spectra of bacteria.

12. The method of claim 10, wherein the absorption spectra is obtained in the regions selected from the group consisting of ultraviolet (UV), visible and infrared (IR).

13. The method of claim 10, wherein the absorption spectra is obtained using an instrument selected from the group consisting of a Fourier transform infrared spectrometer, a fluorometer and a Raman spectrometer.

14. The method of claim 11, wherein the reference spectra is spectra of bacteria selected from the group consisting of *Haemophilus influenzae* (HI), *Morazella catarrhalis* (MC), and *Streptococcus pneumoniae* (SP).

15. The method of claim 10, wherein either dry film or an attenuated reflectance cell are used for analyzing the sample.

16. The method of claim 11, wherein the identity of the bacteria is determined from absorption spectra in the region of 700–1800 $cm^{-1}$.

17. The method of claim 10, wherein the biological fluid sample is selected from the group consisting of blood, saliva, urine, bile, vaginal secretions, middle ear aspirate, pus, pleural effusions, synovial fluid, abscesses, cavity swabs, and serum.

18. A method for the in vivo detection of bacteria comprising the steps of:

a. obtaining the absorption spectra of an uncultured biologic fluid sample directly from a body;

b. subtracting absorption spectra of a reference sample from the absorption spectra of the biologic fluid sample to form a differential spectra;

c. analyzing the differential spectra to detect the presence of bacteria in the sample.

19. The method of claim 18, further comprising the step of:

d. identifying bacteria detected in the biologic fluid sample by comparing the differential spectra with reference spectra of bacteria.

20. The method of claim 18, wherein the absorption spectra is obtained in the regions selected from the group consisting of ultraviolet (UV), visible and infrared (IR).

21. The method of claim 18, wherein the absorption spectra is obtained using an instrument selected from the group consisting of a Fourier transform infrared spectrometer, a fluorometer and a Raman spectrometer.

22. The method of claim 19, wherein the reference spectra is spectra of bacteria selected from the group consisting of *Haemophilus influenzae* (HI), *Morazella catarrhalis* (MC), and *Streptococcus pneumoniae* (SP).

23. The method of claim 18, wherein the biologic fluid sample is selected from the group consisting of a blood, saliva, urine, bile, vaginal secretions, middle ear aspirate, pus, pleural effusions, synovial fluid, abscesses, cavity swabs, and serum.

24. The method of claim 18, wherein the biologic fluid sample is contained in fluid from the human body.

25. The method of claim 19, wherein the identity of the bacteria is determined from absorption spectra in the region of 700–1800 $cm^{-1}$.

26. A method for diagnosing otitis media comprising the steps of:

a. obtaining the absorption spectra directly from an uncultured sample of middle ear aspirate;

b. subtracting the spectrum of a previously-obtained reference sample from the spectra of the middle ear aspirate;

c. analyzing the differential spectra to detect the presence of bacteria in the sample.

* * * * *